United States Patent
Schoenfeldt et al.

(10) Patent No.: US 6,297,423 B1
(45) Date of Patent: Oct. 2, 2001

(54) PERMANENTLY DEFORMABLE DRESSING

(75) Inventors: Lars Schoenfeldt, Snekkersten; Lars Bo Madsen, Gentofte; Jan Marcussen, Taastrup, all of (DK)

(73) Assignee: Colorlast A/S, Humlebaek (DK)

( * ) Notice: Subject to any disclaimer, the term of this patent is extended or adjusted under 35 U.S.C. 154(b) by 0 days.

(21) Appl. No.: 09/147,307

(22) PCT Filed: May 23, 1997

(86) PCT No.: PCT/DK97/00237

§ 371 Date: Nov. 24, 1998

§ 102(e) Date: Nov. 24, 1998

(87) PCT Pub. No.: WO97/45079

PCT Pub. Date: Dec. 4, 1997

(30) Foreign Application Priority Data

May 24, 1996 (DK) .................................................. 0603/96

(51) Int. Cl.[7] ....................................................... A61F 13/00
(52) U.S. Cl. .............................. 602/58; 602/41; 602/42; 602/43; 602/54
(58) Field of Search ........................ 602/41–59; 128/888, 128/889

(56) References Cited

U.S. PATENT DOCUMENTS

| 4,346,700 | 8/1982 | Dunshee et al. . | |
| 4,367,732 | 1/1983 | Poulsen et al. | 128/156 |
| 4,741,949 | 5/1988 | Morman et al. . | |
| 5,051,259 | 9/1991 | Olsen et al. | 424/443 |
| 5,188,124 | * 2/1993 | Fere | 128/889 |
| 5,714,225 | 2/1998 | Hansen et al. | 428/114 |

FOREIGN PATENT DOCUMENTS

| 0 457 977 | 11/1991 | (EP) . |
| 0 676 183 | 10/1995 | (EP) . |
| WO89/05619 | 6/1989 | (WO) . |
| WO94/15562 | 7/1994 | (WO) . |

* cited by examiner

Primary Examiner—Kim M. Lewis
(74) Attorney, Agent, or Firm—Jacobson Holman, PLLC

(57) ABSTRACT

A dressing for covering a portion of the anatomical surface of a living being, said dressing being able to adhere to the skin, the mucosa and/or a wound on any portion of a living being without exposing the skin to a significant stress after application and said dressing showing a permanent deformation created before, during or after application of the dressing and wherein the dressing is optionally covered in part or fully by one or more release liners or cover films to be removed before or during application.

16 Claims, 2 Drawing Sheets

PERMANENTLY DEFORMABLE DRESSING

FIELD OF THE INVENTION

The present invention relates to dressings, in particular dressings for covering a portion of the anatomical surface of a living being, methods for preparing such dressings, the use of a film being able to adhere to the skin for forming such dressings and a method of treating a portion of the anatomical surface of a living being, especially a protruding or retracted part of the body.

BACKGROUND OF THE INVENTION

Conventionally, dressings for the treatment or prevention of wounds or pressure sores or even unbroken skin are essentially flat dressings which are sufficiently mouldable to be applied to flat or slightly curved areas of the body. Such flat dressings are not very suitable for applying on protruding parts of the body or joints such as elbows, heels or especially the tips of fingers or toes or parts of the body having a very pronounced curvature such as the interdigital area as they often wrinkle and focus stresses in the dressing often causing slipping of the adhesive and unintended detachment of the dressing.

Published European patent application No. EP 0 676 183 A1 discloses conformable adhesive bandages which are stated to be extremely conformable, and yet resilient enough to maintain its shape after being subjected to forces caused by movement of the wearer. Furthermore it is stated that the recovered energy of the bandage disclosed in EP 0 676 183 A1 should be relatively high, so as to assure that the bandage will not permanently deform in use. Such recovered energy built-in into a dressing or bandage will inevitably try to retract it to its original shape if stretched during use and expose the skin to a significant stress which will cause nuisance to the user.

U.S. Pat. No. 4,436,700 discloses pressure sensitive adhesive sheet materials, which are stated to be conformable and having viscoelastic properties similar to human skin. Furthermore it is stated, that the materials exhibit stress relaxation with time, having relaxation properties to recover to near original unstressed length, when all stress is removed.

Published European patent application No. EP 0 457 977 A1 discloses a wound dressing comprising a pad of soft polyurethane foam, one surface layer of which is hydrophilic and a backing layer of which is hydrophobic and a sheet or strip of a soft conformable polyether foam having an adhesive on one surface thereof, said dressing showing a sufficient elasticity to readily conform for extended periods of time to difficult areas such as elbow joints and knee joints.

U.S. Pat. No. 1,741,949 discloses an elastic polyetherester nonwoven web formed by meltblowing fibres composed of a polyester.

A liquid plaster in the form of a solution of a polymer in ethyl acetate is known under the trade mark Nobecutan®. Such a plaster will naturally conform to the area onto which it is applied but is highly unsuitable for application on broken or irritated skin due to the content of ethyl acetate giving a severe local irritation.

Until now no reference discloses dressings being able to adhere to the skin, said dressing being flexible and mouldable so as to adapt to the contour of the part of the body to be covered and said dressing adhering to the skin and being able to adapt to and follow the movements of joints such as finger joints without exposing the skin to a significant stress after application and being applicable directly on broken or irritated skin without unpleasant feeling.

One object of the invention is to provide a dressing being mouldable and flexible so as to be able to adapt to the contour of the part of the body to be covered and said dressing adhering to the skin and being able to adapt to and follow the movements of the skin or joints such as finger joints. Such dressing will be suitable as e.g. a finger tip or toe tip dressing or a dressing suitable for use on joints and even in the interdigital area on the hand or foot.

Another object of the invention is to provide a dressing which may prevent e.g. wearing or abrasion damages, e.g. on heels or elbows, said dressing being provided with a surface which may be adapted to the environment in which the dressing is to be used giving a longer effective time of use for the dressing between the change of the dressing.

A further object of the invention is to provide a dressing which comprises emollients or an active constituent e.g. retinoids for treating or preventing formation of psoriasis, eczema, callous skin, corns, insect bites, acne or blisters.

A still further object of the invention is to provide processes for the preparation of such dressings.

BRIEF DESCRIPTION OF THE INVENTION

The invention relates to a dressing for covering a portion of the anatomical surface of a living being, said dressing being able to adhere to the skin, the mucosa and/or a wound on any portion of a living being, and said dressing being mouldable so as to adapt to the contour of the part of the body to be covered.

Furthermore, the invention relates to the use of a film being able to adhere to the skin, said film showing permanent deformation created before or during application of the dressing for forming a dressing for covering a portion of the anatomical surface of a living being.

The invention also relates to a method of treating a portion of the anatomical surface of a living being comprising applying a dressing being able to adhere to the skin, said dressing being mouldable so as to adapt to the contour of the part of the body to be covered.

BRIEF DESCRIPTION OF THE DRAWINGS

The invention is explained more in detail with reference to the drawings in which.

DETAILED DESCRIPTION OF THE INVENTION

Figure 1:
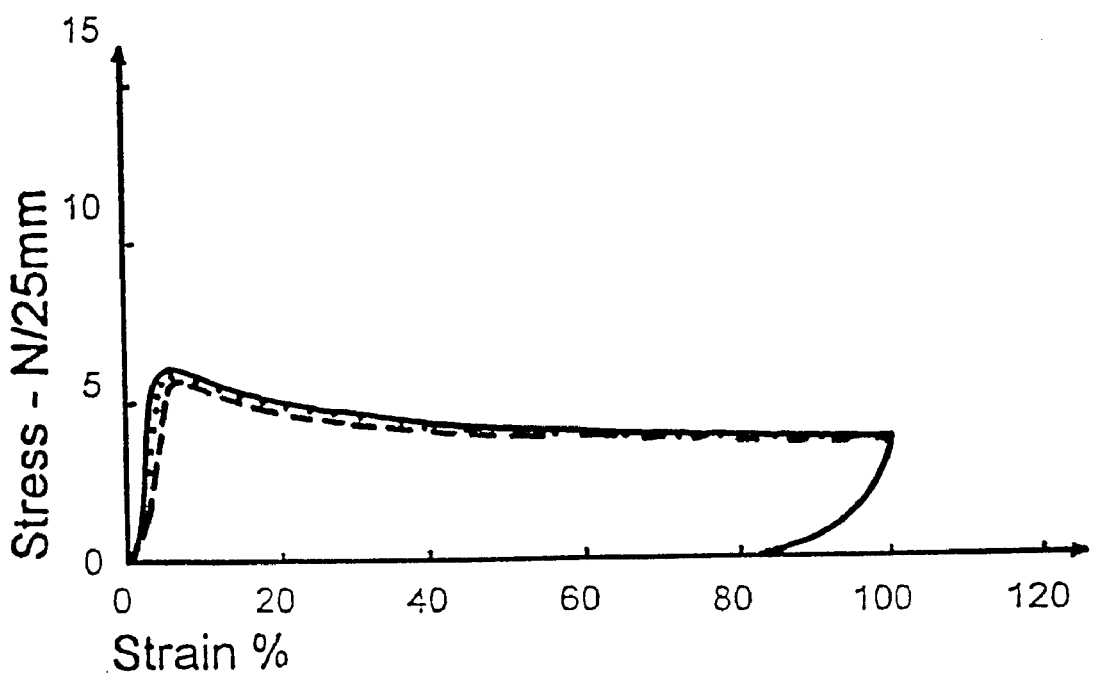
FIG. 1 shows a stress-strain curve for a dressing of the invention subjected to a 100% deformation using a predetermined load whereafter the stress is released.

It has surprisingly been found that the objects of the invention may be fulfilled by a dressing accordingly to the present invention.

The invention relates to a dressing for covering a portion of the surface of a living being, said dressing being able to adhere to the skin, the mucosa and/or a wound on any portion of the living being.

The dressing of the invention is characterised in that it is able to adhere to the skin, the mucosa and/or a wound on any portion of a living being without exposing the site to a significant stress after application and that the dressing shows a permanent deformation created before or during application of the dressing. The dressing is optionally covered in part or fully by one or more release liners or cover films to be removed before or during application.

The dressing of the invention has surprisingly rendered it possible, when applying a dressing to a protruding or essentially flat part of the body to stretch the dressing to suit the size of the part of the body to be covered whereafter the dressing will adapt rather tightly to the contour of the part of the body to be covered and adhere to it without exposing the skin to a significant stress after application. The dressing will adhere to the skin and follow later movements like a "second skin" which will ensure that the dressing does not tauten the skin or constrict parts of the body. The reduced stress will give a long wear time and the dressing of the invention only needs to be changed when it is "technically necessary" and many changes due to slipping are avoided.

Such dressing allows for a stretching of the dressing to be sufficiently deformed to be able to cover a protruding part of the body e.g. a finger, whereafter the dressing quickly adapts to the protruding part of the body and adheres to the same. The dressing of the invention may be wrapped around an extremity such as a finger or stretched to cover e.g. the tip of a finger or a toe or may be stretched before application to an essentially flat area allowing for adaptation of the dressing to the actual portion of the body to be covered. The dressing of the invention is thus very suitable for covering the area between fingers or toes and is also suitable for applying to "irregular" areas suffering from e.g. psoriasis.

According to the invention it is preferred that the stress necessary for producing an elongation of 100% is below 15 N/25 mm, more preferred below 10 N/25 mm and preferably at the most 8 N/25 mm. Such characteristics enable an easy adaptation of the dressing to the area to be covered and ensures that a part of the body is not ligated if wrapped in the dressing.

The thickness is not considered as it is the characteristics of the dressing as such which is decisive; thus, the constituents of the dressing and a dressing of the invention may have a greater thickness given that the dressing fulfils the requirements stated herein.

It is preferred that the elongation at break is at least 100%, preferably at least 200% which allows for a suitable adaptation of the size of the dressing when applying the same, especially when applying and stretching the dressing to cover the tip of the finger or a toe.

In order to ensure a sufficient low stress after application it is preferred that the dressing shows a permanent deformation of at least 60% after having been subjected to elongation of 100%, preferably a permanent deformation of at least 75% after having been subjected to elongation of 100% and suitably a permanent deformation of at least 80% after having been subjected to elongation of 100%.

Normally it is not preferred that the dressing shows a permanent deformation close to 100% after having been subjected to elongation of 100% as it is preferred that a certain elasticity remains allowing the dressing to adapt perfectly to the site by a minor elastic contraction after application.

In one embodiment of the invention the film is inherently adhesive and may be applied directly.

In another embodiment of the invention, a layer of adhesive is applied to at least one surface of the film in order to impart adhesiveness to the film to stick to the site to be covered.

In a special embodiment of the invention, the dressing has at least one area being distinct from the remaining of the dressing. Such area may e.g. function as a marking indicating where to place the part of the body to be covered. This ensures that a protruding part of the body such as the tip of a finger is located correctly before the dressing is stretched to adapt thereto, and a deformation of the dressing beyond the elongation at break is prevented. The marking may be in the form of a visible indication in the form of a mark or a distinct flat or minor three-dimensional part which need not having the stretchable characteristics as stated above for the dressing as such. The area may e.g. have a covering for the release of pressure on pressure wounds. Such covering may e.g. be in the form of a layer of a pad of a foamed material which pad may have central portions which may be removed.

The invention also relates to a method for preparing a dressing for covering a portion of the anatomical surface of a living being, said dressing being able to adhere to the skin, the mucosa and/or a wound on any portion of a living being without exposing the skin to a significant stress after application which method comprises combining an adhesive with a conformable backing layer and a optionally a release liner and optionally a cover film. The combination may be carried out in a manner known per se. During the combination care should be taken that the conformable backing layer and the finished product are not subjected to stresses which will cause an elongation of the layer or finished product.

In a second aspect, the invention relates to the use of a film showing a permanent deformation created before or during application of the film for forming a dressing for covering a portion of the anatomical surface of a living being, said dressing being able to adhere to the skin, the mucosa and/or a wound on any portion of a living being without exposing the skin to a significant stress after application to the skin, said dressing being mouldable so as to adapt to the contour of a protruding part of the body to be covered. When the dressing of the invention is applied to a joint, the dressing may be applied when the joint is in its stretched position whereafter the joint is bended strecheing the dressing. When the dressing is in its streched position it relaxes and will adhere to the skin and follow later movements of the joint like a "second skin".

The surface to be covered with the dressing may be a protruding or retracted part of the body and the dressing is suitable for covering a part of the body having a double-curvature surface as e.g. the interdigital area of a hand or a foot or a joint such as wrist, and elbow, a heel, or a knee.

It is advantageous if the dressing according to the invention comprises wound healing associated indicator(s), cushions or similar device for treatment or prophylaxis of formation of wounds and/or skin abnormalities. This opens for a concomitant medical treatment of the wound and an easy and non-contaminating application of the active ingredients, e.g. by incorporating active ingredients such as a cytochine such as growth hormone or a polypeptide growth factor or retinoids giving rise to the incorporation of such active substances in a form being apt to local application in a wound in which the medicament may exercise its effect on the wound, other medicaments such as bacteriostatic or bactericide compounds, e.g iodine, iodopovidone complexes, chloramine, chlorhexidine, silver salts, zinc or salts thereof, metronidazol, sulpha drugs, and penicillins, tissue-healing enhancing agents, e.g. RGD tripeptides and the like, enzymes for cleansing of wounds, e.g. pepsin, trypsin and the like, cytotoxic agents and proliferation inhibitors for use in for example surgical insertion of the product in cancer tissue and/or other therapeutic agents which optionally may be used for topical application, pain releasing agents, emollients, retinoids or agents having a cooling effect which is also considered an aspect of the invention.

In the present context growth hormone is intended to designate any growth hormone which is applicable in accordance with the invention such as human, bovine, ovine, porcine, equine, salmon or tuna growth hormone or analogues or derivatives thereof such as shortened or extended growth hormones such as methionyl growth hormone. A growth hormone is preferably human growth hormone.

Wound healing associated indicator(s) may e.g. be indicators of pH, partial pressure of $O_2$, temperature, radical mechanisms or biotechnological assays, e.g. indicating formation of collagen.

Furthermore, the invention relates to the use of a "blank" in the form of a film or dressing being able to adhere to the skin, the mucosa and/or a wound on any portion of a living being for forming a dressing being permanently "deformed" to fit the specific area to be covered being differently sized and being larger in at least one dimension than the blank.

In a third aspect, the invention relates to a method of treating a portion of the anatomical surface of a living being comprising applying a dressing showing a permanent deformation created before, during or after application of the dressing for covering a portion of the anatomical surface of a living being, said dressing being able to adhere to the skin, the mucosa and/or a wound on any portion of a living being without exposing the skin to a significant stress after application and wherein the dressing is, optionally covered in part or fully by one or more release liners or cover films to be removed before use, said dressing being applied by placing the same and stretching it so as to cover the part of the body whereafter the dressing is left and adheres to the skin.

A dressing of the invention is typically in the form of a laminate comprising a backing layer, a layer of adhesive and is optionally covered in part or fully by one or more release liners or cover films to be removed before use. The dressing may furthermore comprise a top layer to be removed before use.

The backing layer may be any film or combination of film or layers which, in combination with the adhesive, shows the desired characteristics described above. The film may e.g. be produced from a polyolefinic material or a polyurethane material. A film which is suitable is e.g. the film which is commercially available under the trademark Parafilm®.

The backing layer may e.g. be a combination or laminate of one or more films and/or optionally a fibrous layer such as a woven or non-woven or knitted layer. The backing film may also comprise a fibrous layer such as a woven or non-woven or knitted layer on which a polymeric material has been coated by a manner known per se. Such coating may be present on one or both sides of the film.

The skilled in the art will be able to establish a suitable combination of film and adhesive by routine experiments based on knowledge of the elastic and plastic characteristics of the materials.

The adhesive of a dressing of the invention may be any skin-friendly adhesive known per se being able to adhere to the skin, the mucosa and/or a wound on any portion of a living being and is preferably an adhesive comprising a hydrocolloid. A suitable adhesive is e.g. a hydrocolloid-containing moisture absorbing material such as the adhesive disclosed in U.S. Pat. No. 4,367,732. The adhesive may also comprise a skin friendly acrylate adhesive containing hydrophilic areas. The adhesive may be essentially uniform or be constituted by distinct areas having different composition such as the adhesives disclosed in WO 89/05619 or in WO 94/15562.

The adhesive may comprise fibres which may reinforce the adhesive. A hydrocolloid may be particulate or in the form of fibres.

The living being may be an animal such as a domestic animal such as a horse, a cow or a pig or a pet such as a cat or a dog and is preferably a human being. The top layer may e.g. be a layer of paper or a polymeric film. Any conventional layers, films etc. conventionally used as top layer on a dressing will be suitable as the characteristics of such a top layer of film is not critical for characteristics of the dressing of the invention as it is removed before application of the dressing.

The top layer or the backing layer of the dressing of the invention may provide a surface which shows e.g. abrasion resistance to provide a dressing which may prevent e.g. wearing or abrasion damages, e.g. on heels or elbows, or the top layer or the backing layer of the dressing of the invention may provide surface which shows e.g. hydrophobicity to provide a dressing which is suitable to resist humid environments giving a longer effective time of use for the dressing between the change the dressing.

Release liners which are suitable for use with the dressing of the invention can be made of kraft papers, polyethylene, polypropylene, polyester or composites of any of these materials. The liners are preferably coated with release agents such as fluorochemicals or silicones. The release liner may, if present, be removed before or after application. If only removed after application, the release liner may act as a handle during application.

MATERIALS AND METHODS

Test of a dressing according to the invention as compared to a conventional elastic dressing Test of the physical characteristics according to the invention.

The physical characteristics is documented by the following stress-strain test procedure:

1. A test sample—25×90 mm—was cut out of the dressing to be tested and the release liner is removed before the test. The sample was preconditioned at 23° C. and 50% RH for at least 30 minutes before the test.
2. The preconditioned test sample was mounted between the grips (type TG420 FH) at a Lloyd LR 5K test machine. The initial gate length was 40 mm.
3. The test specimen was extended until 100% strain at a speed of 5 mm/sec. The max. load (N) was measured during this test step.
4. Immediately after reaching 100% strain the test specimen was allowed to retract at a speed of 5 mm/sec. until a load of 0.1 N was reached. The strain at this point defines the permanent deformation.

The test is an indirect control of elongation at break greater than 100%.

EXPERIMENTAL PART

EXAMPLE

Preparation of a dressing according to the invention.

A pressure sensitive hydrocolloid adhesive (PSA) was prepared by compounding 100 g Vistanex® LH-MH (PIB) together with 100 g Blanose 9HXF (CMC) at 130° C. for 30 minutes in a Linden 0.25 lab. mixer.

A laminate consisting of a standard Parafilm® (American Can), the PSA and a release liner (Siliconised paper Sterapap, AC/KV 120, supplied by Jackstadt A/S) was then prepared by heat pressing at 90° C. at a pressure of 150 bar. The laminate was cut into the desired dressing size.

Test of a dressing according to the invention as compared to conventional dressing.

Figure 2:
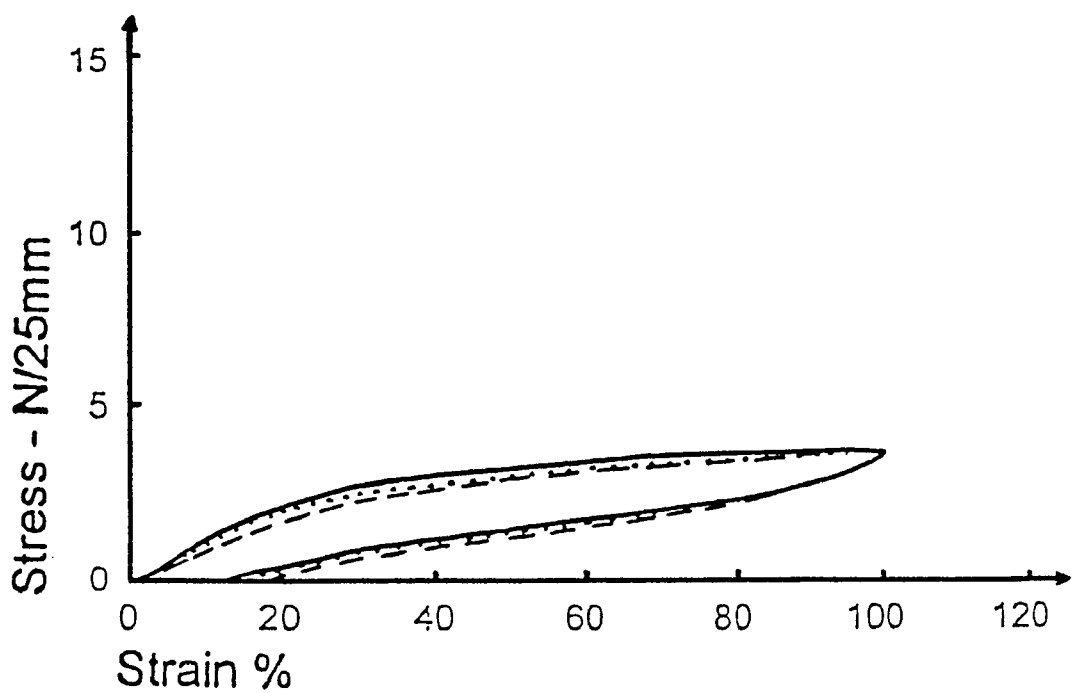
FIG. 2 shows a corresponding stress-strain curve for a conventional dressing (Tegaderm® Transparent Dressing).

FIGS. 1 and 2 show the results of a test as defined above of a dressing according to the invention and of a conventional dressing (Tegaderm® Transparent Dressing from 3M). The curves show the results of three identical experiments each.

It appears from FIG. 1 that a dressing according to the invention shows an initial steep rise of the stress followed by a decrease when further extended until 100% strain. After allowing the specimen to retract until a load of 0.1 N, the dressing of the invention shows a permanent deformation of about 83%.

It appears from FIG. 2 that a conventional dressing shows a quite different stress-strain curve. The stress increases gradually during the extension until 100% strain and the dressing shows a more elastic behaviour and shows a permanent deformation of about 13%.

Test of stress relaxation of a backing film for a dressing according to the invention A standard Parafilm® (American Can) was extended to 20% elongation and the relaxation after 1 minute was determined according to ASTM D882.

The relaxation was about 33% indicating that a dressing according to the invention comprising a backing film having a stress-relaxation characteristic like the standard Parafilm® is able to adhere to the skin, the mucosa and/or a wound on any portion of a living being without exposing the site to a significant stress after application and that the dressing shows a permanent deformation created before or during application of the dressing.

Practical test of a dressing according to the invention.

Blanks were prepared, using a Parafilm® coated with a hydrocolloid adhesive, containing hydrocolloids. They were tested in a group of volunteers (9 individuals, suffering from finger cracks or skin irritation) as compared against a commercially available bandage (Compeed® Cuts & Grazes).

The reports were significant and consistent: All test persons agreed that the tested product was extremely flexible with respect to the freedom of fitting the dressing to a specific injury, regardless the place of injury. A common further remark was "It does not pinch the injury".

The commercially available Compeed® Cuts & Grazes did not show the same degree of flexibility and adaptability as the dressing according to the invention.

What is claimed is:

1. A dressing for covering a portion of the anatomical surface of a living being, said dressing being in the form of a laminate comprising a backing layer and a layer of adhesive able to adhere to the skin, the mucosa and/or a wound on any portion of a living being without exposing the skin to a significant stress after application, said dressing, after being subjected to an elongation in response to a stress applied before or during application thereof, retaining a permanent deformation upon removal of said stress, said deformation being of more than 60% when said dressing has been subjected to elongation of 100%.

2. The dressing as claimed in claim 1, wherein the dressing undergoes an elongation of approximately 100% in response to an applied stress of less than 15 N/inch.

3. The dressing as claimed in claim 2, wherein the dressing undergoes an elongation of approximately 100% in response to an applied stress of less than 10 N/inch.

4. The dressing as claimed in claim 1, wherein the elongation at break is at least 100%.

5. The dressing as claimed in claim 4, wherein the elongation at break is at least 200%.

6. The dressing as claimed in claim 1, wherein the dressing retains a permanent deformation of at least 75% when said dressing has been subjected to elongation of 100%.

7. The dressing as claimed in claim 1 wherein the dressing retains a permanent deformation of at least 85% when said dressing has been subjected to elongation of 100%.

8. The dressing as claimed in claim 1 wherein the dressing has an area distinct from a remainder of the dressing.

9. A method of treating a portion of the anatomical surface of a living being comprising applying a dressing showing a permanent deformation created before or during application of the dressing for covering a portion of the anatomical surface of a living being, said dressing being in the form of a laminate comprising a backing layer and a layer of adhesive and said dressing being able to adhere to the skin, the mucosa and/or a wound on any portion of a living being without exposing the skin to a significant stress after application and wherein the dressing is optionally covered in part or fully by one or more release liners or cover films to be removed before or during application, said dressing being applied by placing the same and stretching it to an elongation of 100% so as to cover the part of the body whereafter the dressing is left and adheres to the skin wherein the force necessary to stretch the dressing to 100% is less than 15 N/inch and thereafter said dressing shows a permanent deformation of at least 60%.

10. The method of treating a portion of the anatomical surface of a living being as set forth in claim 9, wherein the stress necessary for producing the elongation of 100% is below 10 N/inch.

11. The method of treating a portion of the anatomical surface of a living being as set forth in claim 9, wherein the dressing retains a permanent deformation of at least 75% after having been subjected to elongation of approximately 100%.

12. The method of treating a portion of the anatomical surface of a living being as set forth in claim 9, wherein the dressing retains a permanent deformation of at least 85% after having been subjected to elongation of approximately 100%.

13. A dressing for covering an outer surface portion of a living being, said dressing being in the form of a laminate comprising a backing layer and a layer of adhesive able to adhere to the outer surface portion without exposing the outer surface portion to a significant stress during and after application, said dressing, after being elongated in response to a stress applied before or during application thereof, retaining a permanent deformation, and said dressing in response to a stress of less than 15 N/inch capable of being elongated by approximately 100% and thereafter, upon removal of said stress, retaining a permanent deformation of at least 75%.

14. The dressing as set forth in claim 13, wherein said dressing is covered at least in part by one or more release liners or cover films to be removed before or during application.

15. The dressing as claimed in claim 13, wherein the stress necessary for producing an elongation of 100% is below 10 N/inch.

16. The dressing as set forth in claim 13, wherein the dressing retains a permanent deformation of at least 85% when said dressing has been subjected to elongation of 100%.

* * * * *

UNITED STATES PATENT AND TRADEMARK OFFICE
CERTIFICATE OF CORRECTION

PATENT NO. : 6,297,423 B1
DATED : October 2, 2001
INVENTOR(S) : Schoenfeldt et al.

It is certified that error appears in the above-identified patent and that said Letters Patent is hereby corrected as shown below:

<u>Title page,</u>
Item [73], Assignee: the spelling of the name should be corrected from "Colorlast A/S" to -- Coloplast A/S --.

Signed and Sealed this

Eleventh Day of June, 2002

Attest:

JAMES E. ROGAN
*Attesting Officer*    *Director of the United States Patent and Trademark Office*